United States Patent
Butte et al.

(10) Patent No.: US 12,018,082 B2
(45) Date of Patent: Jun. 25, 2024

(54) METHODS AND AGENTS FOR TREATING INFECTIONS

(71) Applicant: The Regents of the University of California, Oakland, CA (US)

(72) Inventors: Manish J. Butte, Los Angeles, CA (US); Maria I. Garcia-Lloret, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 326 days.

(21) Appl. No.: 17/021,280

(22) Filed: Sep. 15, 2020

(65) Prior Publication Data
US 2021/0079104 A1    Mar. 18, 2021

Related U.S. Application Data

(60) Provisional application No. 62/900,894, filed on Sep. 16, 2019.

(51) Int. Cl.
| | | |
|---|---|---|
| *A61K 39/395* | (2006.01) | |
| *A61K 38/21* | (2006.01) | |
| *A61P 31/00* | (2006.01) | |
| *C07K 16/28* | (2006.01) | |

(52) U.S. Cl.
CPC ........ *C07K 16/2866* (2013.01); *A61K 38/217* (2013.01); *A61P 31/00* (2018.01)

(58) Field of Classification Search
CPC .................................................. C07K 16/2866
See application file for complete search history.

(56) References Cited

U.S. PATENT DOCUMENTS

| | | | | |
|---|---|---|---|---|
| 6,039,969 A | * | 3/2000 | Tomai | A61P 29/00 |
| | | | | 424/443 |
| 6,312,924 B1 | * | 11/2001 | Presnell | C07K 14/56 |
| | | | | 435/69.51 |

FOREIGN PATENT DOCUMENTS

| | | | | |
|---|---|---|---|---|
| WO | WO-2010111644 A1 | * | 9/2010 | ............. A61K 31/19 |

OTHER PUBLICATIONS

Perkins et al., "IL-4 induces IL-13-independent allergic airway inflammation", J. Allergy Clin. Immunol., Aug. 2006, 118(2):410-419.
Tsai et al., "Disseminated Coccidioidomycosis Treated with Interferon-γ and Dupilumab", The New England Journal of Medicine, Jun. 11, 2020, 382(24): 2337-2343.

* cited by examiner

*Primary Examiner* — Albert M Navarro
(74) *Attorney, Agent, or Firm* — Mark S. Cohen; Pearl Cohen; ZEDEK LATZER BARATZ LLP

(57) ABSTRACT

Methods are described for treating systemic fungal and mycobacterial infections by treatment to enhances a Th1 response, reduces a Th2 response, or the combination thereof. Agents that antagonize the IL-4, the IL-13 receptor, or the combination thereof achieve the desired results.

10 Claims, 6 Drawing Sheets

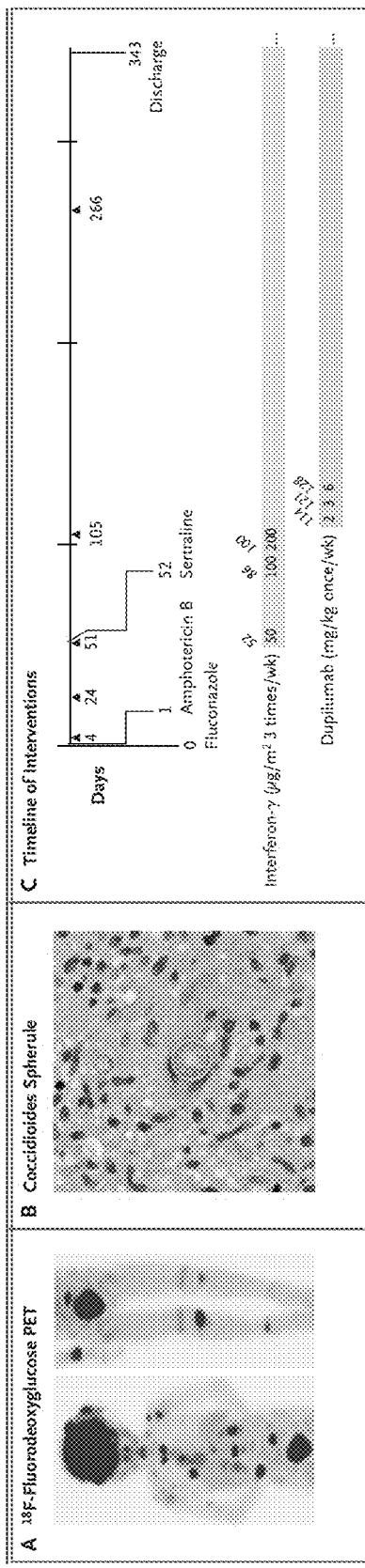

Figures 2A, 2B:
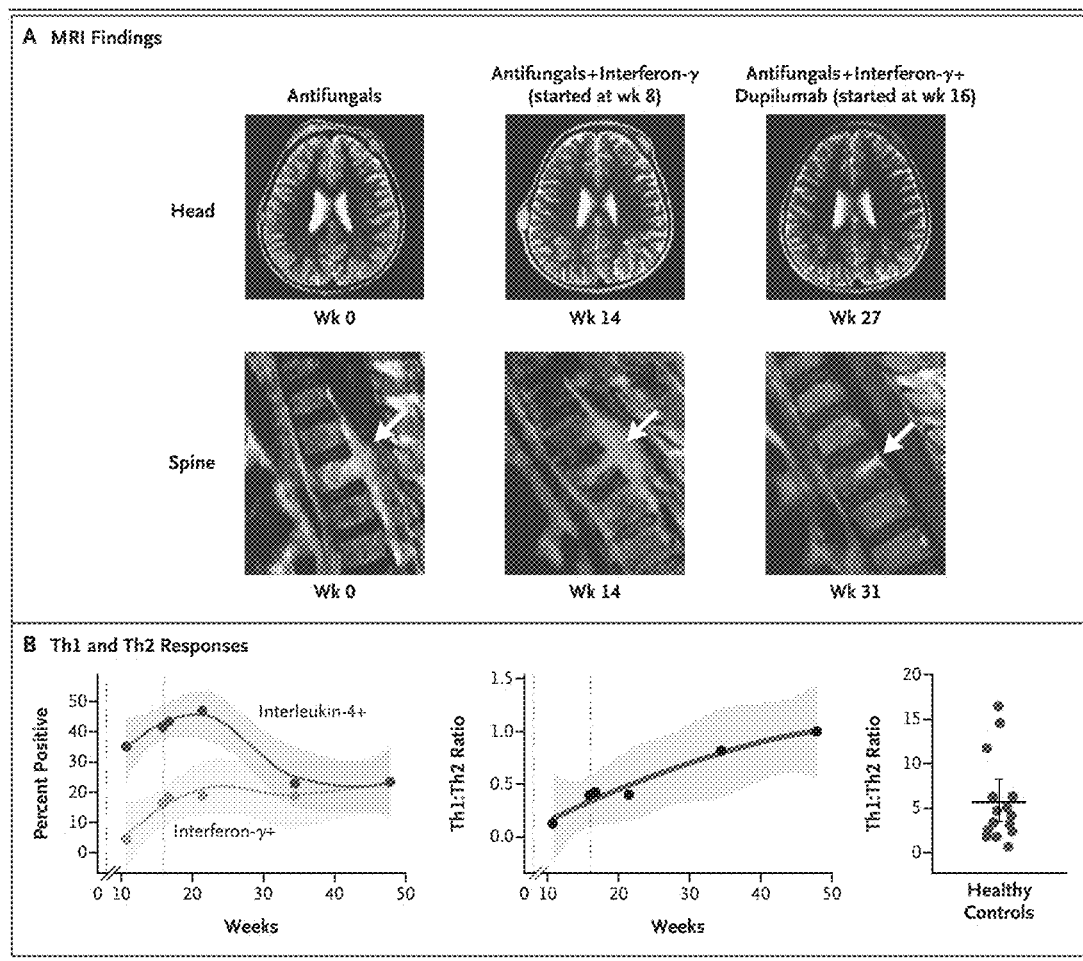

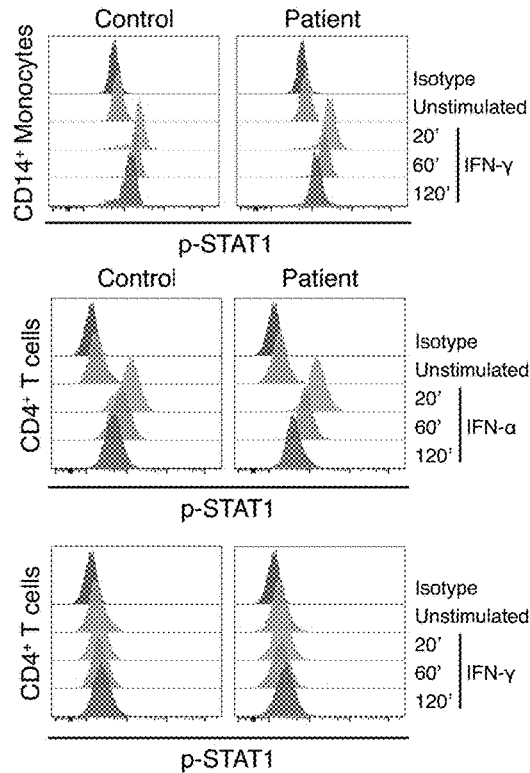
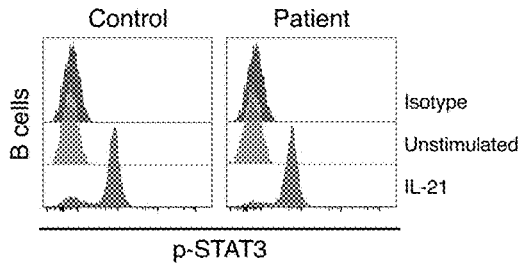
FIG. 3B
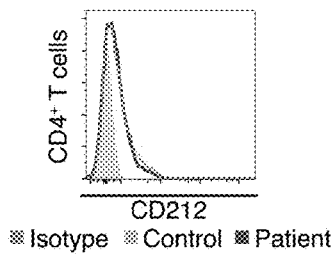
FIG. 3C
FIG. 3A
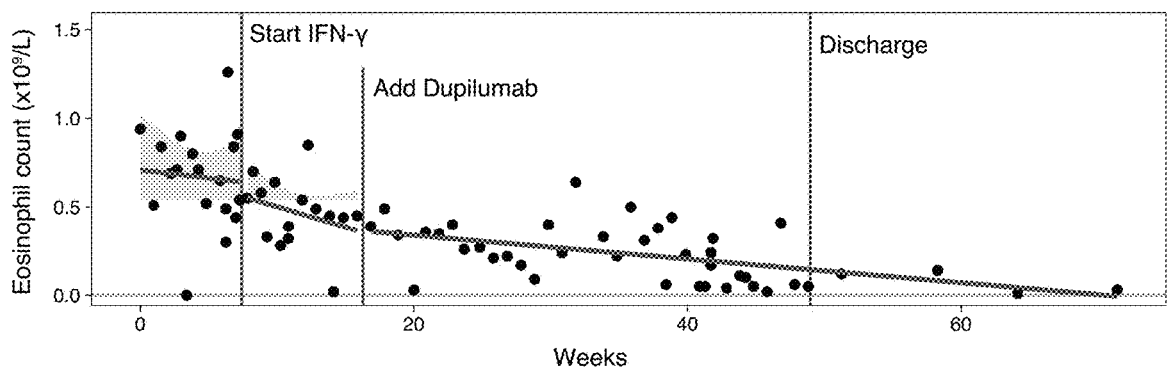
FIG. 3D

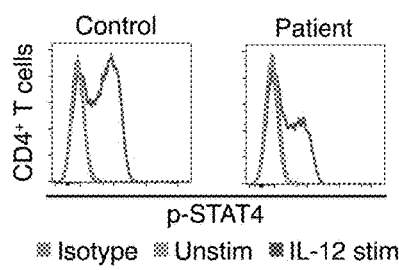
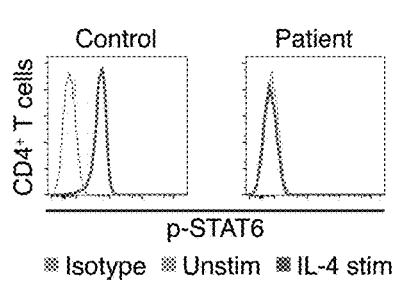
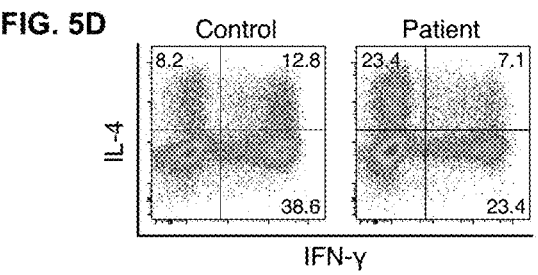
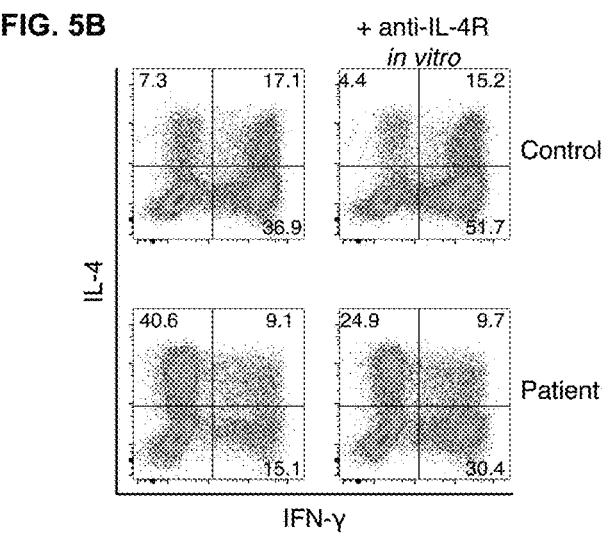

METHODS AND AGENTS FOR TREATING INFECTIONS

CROSS REFERENCE TO RELATED APPLICATION

This application claims benefit of U.S. Provisional Patent Application No. 62/900,894, filed Sep. 16, 2019, which is incorporated by reference herein in its entirety.

GOVERNMENT SUPPORT

This invention was made with government support under Grant Number HG007703, awarded by the National Institutes of Health. The government has certain rights in the invention.

BACKGROUND

Infection with *Coccidioides* fungi is endemic in the Southwestern United States, with an estimated incidence of over 20,000 reported cases per year. Most infections are asymptomatic or cause minor respiratory disease ("Valley Fever"). However, about 1% progress to disseminated coccidioidomycosis (DCM), defined as spread beyond the lungs and often involving the bones, central nervous system, and skin. DCM exacts substantial morbidity with a prolonged disease course, permanent tissue damage, and a fatality rate exceeding 40% despite modern medical and surgical treatments. Treatment of DCM often requires lifelong antifungals, as infections may be chronic or incompletely cleared, indicating an urgent need for new treatments.

Disseminated coccidioidomycosis is especially common in immunosuppressed people. Antifungals may help, but the death rate is very high.

*Mycobacterium* is a bacterial genus of Actinobacteria that includes pathogens known to cause serious diseases in mammals, including tuberculosis (*Mycobacterium tuberculosis*) and leprosy (*Mycobacterium leprae*) in humans. Many other species cause diseases particularly in immunocompromised patients. Mycobacterial infections are notoriously difficult to treat. The organisms are hardy due to their cell wall, which is neither truly Gram negative nor positive. In addition, they are naturally resistant to a number of antibiotics that disrupt cell-wall biosynthesis, such as penicillin. Due to their unique cell wall, they can survive long exposure to acids, alkalis, detergents, oxidative bursts, lysis by complement, and many antibiotics. Most mycobacteria are susceptible to the antibiotics clarithromycin and rifamycin, but antibiotic-resistant strains have emerged. Mycobacterial diseases are especially problematic in immunocompromised patients.

Diseases caused by viruses comprise a vast spectrum including common cold, influenza, chickenpox, human immunodeficiency virus (HIV), and many others. Viruses can affect many areas in the body, including the reproductive, respiratory, and gastrointestinal systems. They can also affect the liver, brain, and skin. Research reveals that that viruses are implicated in many cancers as well. Immunocompromised patients are particularly at risk of serious complications from viral infections.

It is toward new and effective methods for treating fungal, mycobacterial and viral diseases, particularly in immunocompromised patients, that the present invention is directed.

SUMMARY OF THE INVENTION

In one aspect, a method is provided for treating a fungal, mycobacterial or viral infection in a subject in need thereof, comprising administering to the subject an agent that enhances a Th1 response, reduces a Th2 response, or the combination thereof.

In some embodiments, the fungal infection is disseminated or systemic. In some embodiments, the fungal infection is caused by *Coccidioides, Candida, Blastomyces, Histoplasma, Pneumocystis, Paracoccidioides, Talaromyces, Aspergillus, Cryptococcus,* or *Mucorales*. In some embodiments, the systemic fungal infection is coccidioidomycosis.

In some embodiments, the mycobacterial infection is tuberculosis or leprosy.

In some embodiments, the subject is a pediatric subject.

In some embodiments, the subject is immunocompromised. In some embodiments, the subject has an immunodeficiency disease. In some embodiments, the patient shows an exaggerated production of IL-4, a reduced production of IFN-γ, or the combination thereof.

In some embodiments, the agent blocks IL-4 signaling. In some embodiments, the agent blocks IL-13 signaling. In some embodiments, the agent blocks IL-4 and IL-13 signaling. In some embodiments, the agent is an IL-4 receptor antagonist. In some embodiments, the agent is an IL-13 receptor antagonist. In some embodiments, the agent is an IL-4 and IL-13 receptor antagonist. In some embodiments, the agent is an IL-4 receptor alpha antagonist. In some embodiments, the agent is an IL-13 receptor alpha antagonist. In some embodiments, the agent is an IL-13 receptor alpha1 antagonist. In some embodiments, the agent is an antibody or fragment thereof. In some embodiments, the antibody or fragment thereof is a monoclonal antibody or fragment thereof. In some embodiments, the agent is dupilumab, pascolizumab or pitrakinra.

In some embodiments, the agent is co-administered with interferon-gamma.

Thus, in one embodiment, a method for determining whether subject is a candidate for therapy with an agent that enhances a Th1 response, reduces a Th2 response, or the combination thereof, comprising the steps of a. determining the presence of a defect in signaling related to interferon-gamma, STAT1, STAT3 or STAT4, and b. if a defect in signaling is determined, initiating therapy. In one embodiment, the defect is determined by measuring responses of the subject's monocytes or T cells to stimulation interferon-alpha, interferon-gamma, IL-21, or IL-12. Therapy comprises any of the agents or combinations thereof described herein.

In one embodiment, a method for determining whether subject is a candidate for therapy with an agent that enhances a Th1 response, reduces a Th2 response, or the combination thereof, comprising the steps of a. determining the presence of a genetic defect in IL12RB1, IL12RB2 or TYK2 genes or any PID gene, and b. if a genetic defect in is determined, initiating therapy. In one embodiment, the Therapy comprises any of the agents or combinations thereof described herein.

In one embodiment, a method for determining whether subject is responding to therapy with an agent that enhances a Th1 response, reduces a Th2 response, or the combination thereof, comprising determining the signaling of the IL-12 receptor, the proportion of Th1 cells, or both, wherein improved IL-12 receptor signaling or increased proportion of Th1 cells indicates effectiveness of therapy. Therapy comprises any of the agents or combinations thereof described herein.

In one embodiment, a method for determining whether subject is a candidate for therapy with an agent that enhances a Th1 response, reduces a Th2 response, or the combination thereof, comprising incubating the subject's T cells with the agent and measuring the ratio or interferon-gamma to IL-4 producing helper T cells, wherein an increase in the ratio indicates potential effectiveness of therapy. Therapy comprises any of the agents or combinations thereof described herein.

In one embodiment, a method for determining whether therapy with an agent that enhances a Th1 response, reduces a Th2 response, or the combination thereof, is effective in a subject comprising determining the ratio of polyclonal Th1 to Th2 cells, wherein an increased ratio indicates improvement. Therapy comprises any of the agents or combinations thereof described herein.

In one embodiment, a method for determining whether therapy with an agent that enhances a Th1 response, reduces a Th2 response, or the combination thereof, is effective in a subject with disseminated coccidiomycosis, comprising determining the ratio of cocci-specific Th1 to Th2 cells, wherein an increased ratio indicates effectiveness. Therapy comprises any of the agents or combinations thereof described herein.

BRIEF DESCRIPTIONS OF THE FIGURES

FIGS. 1A-F describe a case of disseminated coccidioidomycosis characterized by defective IL-12 signaling and Th1 response. FIG. 1A. $^{18}$F-fluorodeoxyglucose positron-emission tomographic (PET) scan showing disseminated infection with multiple lesions of the spine, clavicle, ribs, paratracheal lymph nodes, right distal radius, and right leg. FIG. 1B. *Coccidioides* spherule obtained from surgical biopsy of scalp lesion. FIG. 1C. Timeline of interventions in our patient. Initial treatment included fluconazole and liposomal amphotericin B, and sertraline was added at day 52 after admission. Treatment with subcutaneous interferon-γ was also started on day 52, and treatment with dupilumab was started on day 114. Triangles represent major debridement surgical procedures. Doses of IFN-γ and Dupilumab are indicated in the shaded bars; numbers above the bars are days after admission. FIG. 1D. Stimulation of helper T-cell blasts with IL-12, which led to a poor phosphorylated STAT4 (pSTAT4) response, but the loss of function was not absolute (arrow). FIG. 1E. Intracellular cytokine staining of CD4+ T-cell effectors generated in neutral conditions and stimulated with phorbol myristate acetate (PMA) and ionomycin. IL-4 production was greatly enhanced relative to IFN-γ production in the patient as compared with a control. A normal response was only partially restored by culturing in type 1 helper T (Th1) cell conditions (i.e., with IL-12). FIG. 1F. Stimulation of PBMC with T27K coccidioidal antigen, which led to increased production of IL-4 over IFN-γ in helper T cells.

FIGS. 2A-B depict the resolution of disseminated coccidioidomycosis upon treatment with IFN-γ and dupilumab. FIG. 2A. MRI of the head and spine at baseline and during treatment. A spinal lesion is indicated by the arrow. FIG. 2B. Percentage of CD4+ T cells producing IFN-γ (Th1 cells) or IL-4 (Th2 cells) (left) and their ratio (center) over time. The ratio does not include double positive (i.e., positive for IFN-γ and IL-4) cells. The first dashed line represents the initiation of IFN-γ treatment, and the second dashed line represents the initiation of dupilumab treatment. Shading indicates the 95% confidence interval. For comparison, the Th1:Th2 ratio for 15 healthy controls is shown (right). The horizontal line indicates the bootstrapped mean, and the I bar indicates the 95% confidence level.

FIGS. 3A-D depict normal responses of STAT1 and STAT3 in the proband. FIG. 3A. Peripheral blood cells were stimulated with IFN-α and IFN-γ and phosphorylation of STAT1 evaluated by flow cytometry as a function of time. FIG. 3B. Peripheral blood B cells from the patient or a healthy control were stimulated with IL-21 and phosphorylation of STAT3 evaluated by flow cytometry. FIG. 3C. Expression of CD212 (IL12RB1) by flow cytometry. FIG. 3D. Patient's absolute eosinophil counts over time.

Figure 4A:
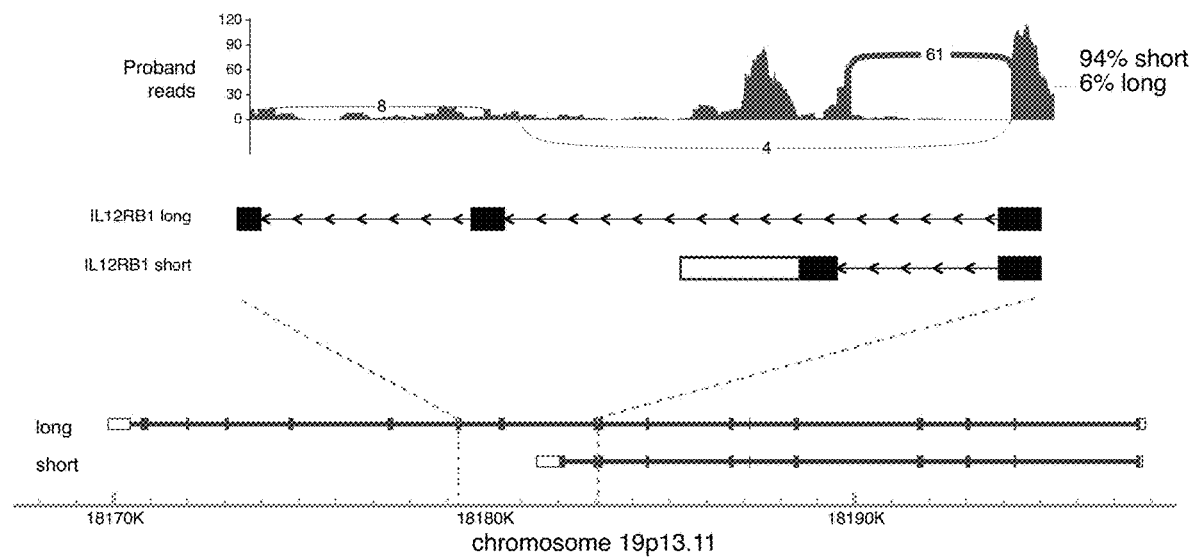
Figure 4B:
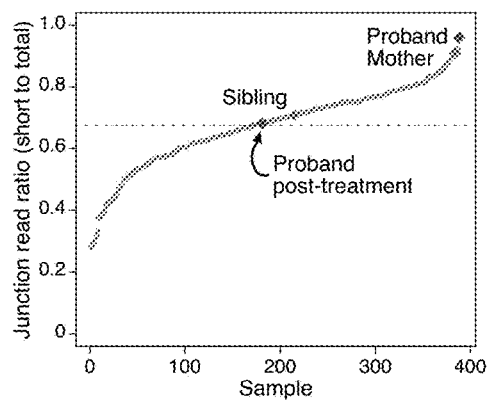
Figure 4C:
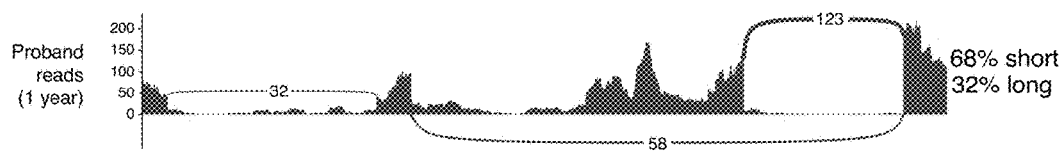

FIGS. 4A-C depict transcriptional differences in the proband. FIG. 4A. Sashimi plot showing the two transcripts of the IL12RB1 gene (short and long). FIG. 4B. Gray dots show the proportion of the IL12RB1 transcripts of the short isoform compared to total IL12RB1 transcripts from RNA-sequencing of whole blood cells from 387 non-immunodeficient individuals. Superimposed on the plot is the percentage of short transcripts for the proband. The healthy controls had an average of 67.4%±12.8% short isoform (mean±SD, dashed line), giving the proband's transcript a Z-score of 2.22. FIG. 4C. Sashimi plot showing the proband's whole blood transcripts of IL12RB1 one year after treatment with IFN-γ and dupilumab, including reads spanning the exon-exon junctions of the short and long isoforms.

FIGS. 5A-D depict immunological responses to treatment. FIG. 5A. Improved response to IL-12 stimulation in CD4+ T cell effectors after initiation of treatment with IFN-γ. FIG. 5B. Enhanced IFN-γ production and decreased IL-4 production in CD4+ T cell effectors cultured with dupilumab ex vivo. FIG. 5C. Peripheral blood CD4+ T cells from the patient while on dupilumab or a healthy, untreated control subject were stimulated with IL-4 and phosphorylation of STAT6 shown. FIG. 5D. Normalization of Th1 and Th2 cells after treatment with IFN-γ and dupilumab.

Figure 6A:
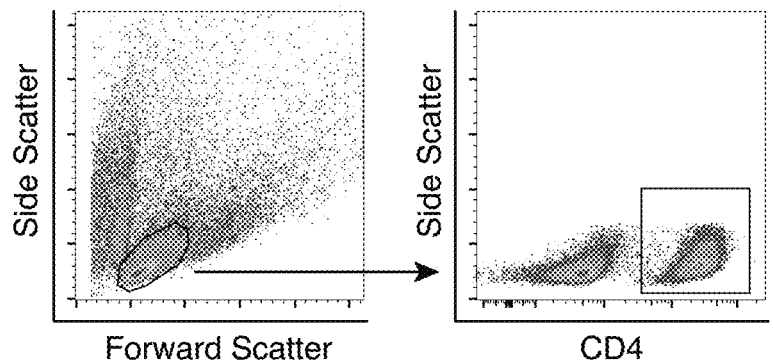
Figure 6B:
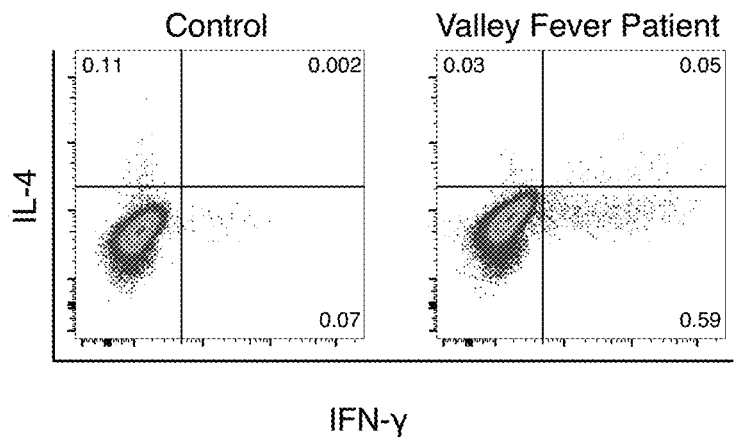

FIGS. 6A-B. Control Valley Fever patient produces a Th1 response to stimulation with *Coccidioides* antigen. FIG. 6A shows gating strategy for experiments where PBMC were stimulated with *Coccidioides* antigen (see FIG. 1F). FIG. 6B. Stimulation of PBMC from a patient who had recovered from Valley Fever with T27K *Coccidioides* antigen revealed an exclusively Th1 response.

DETAILED DESCRIPTION OF THE INVENTION

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure, the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value.

Similarly, when values are expressed as approximations, by use of the antecedent "about," it is understood that the particular value forms another embodiment. All ranges are inclusive and combinable. In the context of the present disclosure, by "about" a certain amount it is meant that the amount is within ±20% of the stated amount, or preferably within ±10% of the stated amount, or more preferably within ±5% of the stated amount.

As used herein, the terms "treat", "treatment", or "therapy" (as well as different forms thereof) refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. Those in need of treatment include those already with the disease or condition as well as those prone to having the disease or condition or those in which the disease or condition is to be prevented.

As used herein, the terms "component," "composition," "formulation", "composition of compounds," "compound," "drug," "pharmacologically active agent," "active agent," "therapeutic," "therapy," "treatment," or "medicament," are used interchangeably herein, as context dictates, to refer to a compound or compounds or composition of matter which, when administered to a subject (human or animal) induces a desired pharmacological and/or physiologic effect by local and/or systemic action. A personalized composition or method refers to a product or use of the product in a regimen tailored or individualized to meet specific needs identified or contemplated in the subject.

The terms "subject," "individual," and "patient" are used interchangeably herein, and refer to an animal, for example a human, to whom treatment with a composition or formulation in accordance with the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys. The compositions described herein can be used to treat any suitable mammal, including primates, such as monkeys and humans, horses, cows, cats, dogs, rabbits, and rodents such as rats and mice. In one embodiment, the mammal to be treated is human. The human can be any human of any age. In an embodiment, the human is an adult. In another embodiment, the human is a child. The human can be male, female, pregnant, middle-aged, adolescent, or elderly. According to any of the methods of the present invention and in one embodiment, the subject is human. In another embodiment, the subject is a non-human primate. In another embodiment, the subject is murine, which in one embodiment is a mouse, and, in another embodiment is a rat. In another embodiment, the subject is canine, feline, bovine, equine, laprine or porcine. In another embodiment, the subject is mammalian.

Conditions and disorders in a subject for which a particular drug, compound, composition, formulation (or combination thereof) is said herein to be "indicated" are not restricted to conditions and disorders for which that drug or compound or composition or formulation has been expressly approved by a regulatory authority, but also include other conditions and disorders known or reasonably believed by a physician or other health or nutritional practitioner to be amenable to treatment with that drug or compound or composition or formulation or combination thereof.

The inventors herein have found that blocking Type-2 immunity can treat infection. This immunomodulatory approach could be used to enhance immune clearance of refractory fungal, mycobacterial, and viral infection. In one embodiment, successful treatment by blocking Type-2 immunity was successful in a case of life-threatening, disseminated coccidioidomycosis (DCM) in a previously healthy child. Like most patients with DCM, this child lacked genomic evidence of any rare immune disease. However, comprehensive immunological testing showed an exaggerated production of IL-4 and reduced production of IFN-γ. Supplementation of antifungals with IFN-γ treatment slowed disease progression and the addition of IL-4/IL-13 blockade resulted in rapid clinical resolution. This approach may be used to treat infections in particular when the patient is immunocompromised or shows an exaggerated production of IL-4, reduced production of IFN-γ, or the combination thereof.

Risk factors for DCM include pregnancy, immuno suppression, HIV/AIDS, and monogenic defects of the IL-12/IFN-γ axis2, all states where immune responses of Type-2 immunity dominate over Type-1. The inventors herein found that treatment with IFN-γ (augmenting Type-1 immunity) in combination with dupilumab (suppressing Type-2 immunity) resulted in complete resolution in a patient with life-threatening DCM and who bore no identifiable, monogenic immunodeficiency. These observations show that a relative insufficiency of Type-1 immunity combined with strong Type-2 responses confers susceptibility to DCM. Restoring the balance between Type-1 and Type-2 immunity enables clinical improvement, and that the relative differentiation state of T helper cells may serve as a useful biomarker in this disease. Moreover, other fungal as well as mycobacterial diseases in particular in immunocompromised individuals are further uses of the methods described herein.

In some embodiments, suppressing type-2 immunity alone enables clinical improvement.

Type-1 helper T cells (Th1) produce IFN-γ, which augments microbial killing by macrophages and other innate cells. Patients with DCM show a direct correlation between disease resolution and production of IFN-γ by lymphocytes in response to *Coccidioides* antigen. Consequently, IFN-γ has been used with success as adjunctive therapy in a few cases of DCM. In our study, however, this approach was insufficient to abate disease despite the improvement of IL-12 signaling and some restoration of helper T cell differentiation.

Type-2 responses may be deleterious in coccidioidomycosis in animal models. IL-4 suppresses Th1 development and reduces antifungal activity of phagocytes and neutrophils. We therefore reasoned that inhibiting the Th2 milieu could halt the relentless dissemination of the patient's disease. Indeed, addition of dupilumab accelerated clinical improvement with resolution of bone and soft tissue lesions.

The complement fixation titers became undetectable and inflammatory markers normalized.

In the studies described here, exome and genome sequencing failed to identify any plausible rare variants to explain a susceptibility to DCM. Pathogenic variants are expected to be rare because genes required for fitness usually fall under purifying selection, but only when selective pressures are universal. Outside the narrow region where *Coccidioides* is endemic, selective pressures on genes that confer susceptibility to DCM may be minimal. Thus, a not-so-rare variant may be pathogenic for subjects exposed to *Coccidioides*. Indeed, we now know that not-so-rare variants explain susceptibility to tuberculosis, another "Th1 disease." RNA sequencing from whole blood picked up both the short and long transcriptional isoforms of IL12RB1. The short isoform cannot respond to cytokines because it lacks its signaling domain and localizes in an intracellular compartment. In the patient described here, the ratio of short to long isoforms was 25:1, whereas in healthy humans the mean ratio is ~2:1. We speculate in this case a non-rare genomic variant or epigenetic change drove aberrant splicing, which was rescued by activation through IFN-γ-STAT1 signaling and thereby promoted expression of the longer isoform.

Thus, this use of dupilumab provides a treatment for infection. In combination with IFN-γ, dupilumab served as a pivotal adjunctive therapy in the treatment of DCM. This immunomodulatory approach has therapeutic potential for other severe fungal, mycobacterial, and viral infections.

Moreover, systemic infections especially in immunocompromised patients are difficult to treat. The inventors have discovered that the immune system can be manipulated to successfully treat such infections by administering to the patient certain immunomodulatory drugs. In one embodiment, by skewing the immune response away from a Th2 response (allergic type T cells) response and towards a Th1 response (a pro-inflammatory response, producing mainly gamma-interferon), treatment of the infection can be achieved. In one embodiment, by targeting interleukin-4 (IL-4) and/or interleukin-13 (IL-13), this shift in the immune response may be achieved.

In one embodiment, administering an agent that blocks IL-4 signaling achieves the desired shift in the immune response. In one embodiment, and IL-4 receptor antagonist may be used. In one embodiment, an antibody that targets the IL-4 receptor may be used. In one embodiment, an antibody that targets the IL-4 receptor alpha subunit may be used. In one embodiment, the antibody may be a monoclonal antibody. In one embodiment, the monoclonal antibody is dupilumab.

In one embodiment, by targeting interleukin-13 (IL-13), this shift in the immune response may be achieved. In one embodiment, administering an agent that blocks IL-13 signaling achieves the desired shift in the immune response. In one embodiment, and IL-13 receptor antagonist may be used. In one embodiment, an antibody that targets the IL-13 receptor may be used. In one embodiment, an antibody that targets the IL-13 receptor alpha subunit may be used. In one embodiment, an antibody that targets the IL-13 receptor alpha1 subunit may be used. In one embodiment, the antibody may be a monoclonal antibody. In one embodiment, the monoclonal antibody is dupilumab.

In one embodiment, by targeting both interleukin-4 (IL-4) and interleukin-13 (IL-13), this shift in the immune response may be achieved. In one embodiment, administering one or more agents that block both IL-4 and IL-13 signaling achieves the desired shift in the immune response. In one embodiment, an IL-4 and IL-13 receptor antagonist may be used. In one embodiment, an IL-4 receptor antagonist and an IL-13 receptor1 antagonists may be used. In one embodiment the antagonist or antagonists are monoclonal antibodies. In one embodiment, the antibodies may be a monoclonal antibody. In one embodiment, the monoclonal antibody is dupilumab.

Dupilumab (DUPIXENT) is a monoclonal antibody indicated for treatment of atopic dermatitis, and studies are ongoing for the treatment of asthma. It inhibits signaling of interleukin-4 (IL-4) and interleukin-13 (IL-13). A course of dupilumab therapy for atopic dermatitis in adults may comprise an initial dose of 600 mg (two 300 mg subcutaneous injections in different injection sites), followed by 300 mg intravenously given every other week. For treatment of atopic dermatitis in adolescents, for an adolescent less than 60 kg, an initial dose of 400 mg (two 200 mg subcutaneous injections) followed by 200 mg subcutaneously every other week. For an adolescent of 60 kg or more, an initial dose of 600 mg (two 300 mg subcutaneous injections) followed by 300 mg subcutaneously every other week. For treatment of asthma in adults and adolescents 12 years of age or older, an initial dose of 400 mg (two 200 mg subcutaneous injections) followed by 200 mg give every other week; or an initial dose of 600 mg (two 300 mg subcutaneous injections) followed by 300 mg given every other week. In one embodiment, these dosing regimens may be followed for subjects with an infection as described herein.

Other agents that inhibit signaling of IL-4 useful for the purposes herein include pascolizumab and pitrakinra (AEROVANT).

Pascolizumab is a humanized antibody that neutralizes the effects of IL-4. Pitrakinra is a 15-kDa human recombinant protein of wild-type human interleukin-4 (IL-4). It is an IL-4 and IL-13 antagonist that has been studied in a phase IIb clinical trial for the treatment of asthma.

Pitrakinra is a mutant form of recombinant human IL-4. Two-point mutations on pitrakinra (position 121 mutated from arginine to aspartic acid and position 124 mutated from tyrosine to aspartic acid) confer its ability to block signaling of IL-4 and interleukin-13 (IL-13) by preventing assembly of IL-4 receptor alpha (IL-4Rα) with either IL-2Rγ or IL-13Rα.

The receptor for interleukin-4 is known as the IL-4Rα. This receptor exists in 3 different complexes throughout the body. Type 1 receptors are composed of the IL-4Rα subunit with a common γ chain and specifically bind IL-4. Type 2 receptors consist of an IL-4Rα subunit bound to a different subunit known as IL-13Rα1. These type 2 receptors have the ability to bind both IL-4 and IL-13, two cytokines with closely related biological functions.

Agents that inhibit signaling of IL-13 useful for the purposes herein include antibodies including monoclonal antibodies to the IL-13 receptor, the 11-13 alpha receptor or the IL-13 alpha1 receptor. Other agents that inhibit IL-13 signaling include the IL-13 antagonist, soluble IL13Ra2-Fc. Other agents useful for the practice of the invention include lebrikizumab, anrukinzumab, and tralokinumab.

The activity of IL-13 is mediated through binding to two different cytokine receptor chains that form a heterodimer expressed on IL-13-responsive cells: the IL-13R-α1 and the IL-4R-α chains. This receptor is activated by both IL-13 and by IL-4. While antagonists of IL-4 and IL-13 exist and are useful for the purposes herein, antagonists specific for only IL-4, or specific only IL-13, are also useful for the purposes herein. In one embodiment, an agent of the invention inhibits only IL-13 signaling. In one embodiment, and agent of the invention inhibits only IL-4 signaling. In one embodiment, and agent of the invention inhibits both IL-4 and IL-13 signaling.

The subject may also be administered interferon-gamma with the agents described herein. In one embodiment, the subject may be administered a dose of between 50 and 200 µg/m².

In some embodiments, the subject is a pediatric subject. In some embodiment the subject is an adolescent patient. In some embodiments the subject is an adult patient. In some embodiments the subject is 12 years of age or less. In some embodiments the subject is 6 years of age or less. In some embodiments the subject is 3 years of age or less. In some embodiments the subject is over 12 years of age.

In one embodiment, the methods described herein are useful for treating infections in patients with an immunodeficiency. Such immunodeficiencies may be inborn or acquired. Most cases of immunodeficiency are acquired ("secondary") due to extrinsic factors that affect the patient's immune system. Examples of these extrinsic factors include HIV infection, extremes of age, and environmental factors, such as nutrition. In the clinical setting, the immunosuppression by some drugs, such as steroids, can be either an adverse effect or the intended purpose of the treatment. Examples of such use is in organ transplant surgery as an anti-rejection measure and in patients suffering from an overactive immune system, as in autoimmune diseases. Some people are born with intrinsic defects in their immune system, or primary immunodeficiency. A person who has an immunodeficiency of any kind is said to be immunocompromised. In one embodiment, an immunocompromised person may be particularly vulnerable to opportunistic infections, in addition to normal infections that could affect everyone.

In treating a severely ill child who presented with coccidioidomycosis in hospital, the inventors sought to skew the patient's immune system away from a Th2 response, in which allergic type T cells are generates, to a Th1 response, where gamma-interferon is produced. The child was treated with dupilumab (2 mg/kg weekly and up-titrated to 6 mg/kg weekly) and the infection was successfully treated.

Similarly, other systemic fungal infections such as systemic candidiasis, infections with *Blastomyces, Histoplasma, Pneumocystis, Paracoccidioides, Talaromyces* spp., *Aspergillus, Cryptococcus, Mucorales* spp., may be treated following the guidance herein.

Mycobacterial infections are also treatable by the methods described herein. Such infections include tuberculosis, leprosy, and *M. bovis, M. africanum*, and *M. microti*. Infection by other mycobacterial species of humans and animals are also treatable by the methods described herein.

Viruses causing human and other mammalian infections are numerous and are especially problematic in immunocompromised individuals. The teachings herein are applicable to the treatment of subjects having a viral infection, in particular in immunocompromised subjects.

In some embodiments, the virus comprises a virus from the Coronaviridae family, the Arenaviridae family, the Nairoviridae family, the Flaviviridae family, the Hepeviridae family, the Filoviridae family, or the Togaviridae family.

In some embodiments, the virus from the Coronaviridae family comprises human coronavirus 229E (HCoV-229E), Middle East respiratory syndrome coronavirus (MERS-CoV), severe acute respiratory syndrome coronavirus (SARS-CoV), severe acute respiratory syndrome coronavirus 2 (SARS-CoV-2, COVID-19 virus), human coronavirus OC43 (HCoV-OC43), human coronavirus NL63 (HCoV-NL63), or human coronavirus HKU1 (HCoV-HKU1).

In some embodiments, the virus from the Arenaviridae family comprises Lassa mammarenavirus (LAS V), Guanarito mammarenavirus, Junin mammarenavirus, Lujo mammarenavirus, Machupo mammarenavirus, Sabia mammarenavirus, or Whitewater Arroyo mammarenavirus.

In some embodiments, the virus from the Nairoviridae family comprises Crimean-Congo hemorrhagic fever virus (CCHFV).

In some embodiments, the virus from the Flaviviridae family comprises Zika virus (ZIKV), hepacivirus C (hepatitis C virus, HepC), dengue fever virus, yellow fever virus, Japanese encephalitis virus, or West Nile virus.

In some embodiments, the virus from the Hepeviridae family comprises hepatitis E virus (HEV) or hepatitis B virus.

In some embodiments, the virus from the Filoviridae family comprises Ebolavirus, Marburgvirus, Dianlovirus, Cuevavirus, Striavirus, or Thamnovirus.

In some embodiments, the virus from the Togaviridae family comprises an Alphavirus. In some embodiments, the virus from the Alphavirus comprises Chikungunya virus, Eastern equine encephalitis virus, Western equine encephalitis virus, Barmah Forest virus, Mayaro virus, O'nyong'nyong virus, Ross river virus, Semliki Forest virus, Sindbis virus, Una virus, Tonate virus, or Venezuelan equine encephalitis.

In some embodiments, the virus comprises a virus from the Adenoviridae, Herpesviridae, Papovaviridae, Paramyxoviridae, Parvoviridae, Picornaviridae, Rhabdoviridae, or Poxviridae families.

In some embodiments, the virus from the Adenoviridae family comprises common cold and other respiratory disease viruses.

In some embodiments, the virus from the Herpesviridae family comprises Herpes simplex virus, varicella-zoster virus, cytomegalovirus, or Epstein-Barr virus.

In some embodiments, the virus from the Parviviridae family comprises parvovirus.

In some embodiments, the virus from the Papovaviridae family comprises human papilloma virus.

In some embodiments, the virus from the Poxviridae family comprises smallpox virus, cowpox, myxoma virus, monkeypox, or vaccinia virus.

In some embodiments, the virus from the Picornaviridae family comprises polio virus.

In some embodiments, the virus from the Paramyxoviridae family comprises measles virus and mumps virus.

In some embodiments, the virus from the Rhabdoviridae family comprises rabies virus.

In some embodiments, the virus comprises a virus from the Retroviridae family, such as HIV.

The aforementioned viruses and virus families are merely non-limiting examples of the use of the methods described herein to treat viral infections, including in immunocompromised individuals. Other viral disease amenable to the methods set forth herein are described in Strauss JH and Strauss EG. Viruses and Human Diseases. Elsevier Inc., Academic Press, 2008, ISBN 978-0-12-373741-0, incorporated herein by reference.

Furthermore, diagnostic tests may be employed to determine the need for Th2 therapy as described herein, and when the T helper balance is being or has been restored and therapy may be reduced or discontinued. In one embodiment, monocytes or T cells from the patient may be evaluated for responses to stimulation interferon-alpha, interferon-gamma, IL-21, or IL-12 to determine if there is a defect in signaling related to interferon-gamma, STAT1, STAT3 or STAT4. Identification of defective signaling would indicate that blocking Type-2 immunity would be beneficial. In another embodiment, a genetic defect in IL-12 receptor signaling may be identified, such as by the presence of variants in the IL12RB1, IL12RB2 or TYK2 genes or any PID gene. Identification of defective gene indicates that blocking Type-2 immunity would be beneficial.

In another embodiment, the efficacy of treatment as described herein can be evaluated by measuring signaling of the IL-12 receptor, the proportion of Th1 cells, wherein improved IL-12 receptor signaling, increased proportion of Th1 cells, or both, indicate an improvement. In another embodiment, the level of inflammatory markers provides an indication of the treatment. In another embodiment, the shift in T helper cells by an agent described here may be evaluated in vitro to predict efficacy in vivo. In one embodiment, a patient's T cells are incubated with dupilumab, and the ratio of interferon-gamma-producing to IL-4-producing helper T cells is determined. An increase in the ratio indicates potential benefit of treatment, and treatment may be started. In another embodiment, the ratio of polyclonal Th1 to Th2 cells can be determined, as well as, in the case of DCM, the ratio of cocci-specific T cells. An increase in ratios indicates improvement.

Thus, in one embodiment, a method for determining whether subject is a candidate for therapy with an agent that enhances a Th1 response, reduces a Th2 response, or the combination thereof, comprising the steps of a. determining the presence of a defect in signaling related to interferon-gamma, STAT1, STAT3 or STAT4, and b. if a defect in signaling is determined, initiating therapy. In one embodiment, the defect is determined by measuring responses of the subject's monocytes or T cells to stimulation interferon-alpha, interferon-gamma, IL-21, or IL-12. Therapy comprises any of the agents or combinations thereof described herein.

In one embodiment, a method for determining whether subject is a candidate for therapy with an agent that enhances a Th1 response, reduces a Th2 response, or the combination thereof, comprising the steps of a. determining the presence of a genetic defect in IL12RB1, IL12RB2 or TYK2 genes or any PID gene, and b. if a genetic defect in is determined, initiating therapy. In one embodiment, the Therapy comprises any of the agents or combinations thereof described herein.

In one embodiment, a method for determining whether subject is responding to therapy with an agent that enhances a Th1 response, reduces a Th2 response, or the combination thereof, comprising the steps of a. determining the signaling of the IL-12 receptor, the proportion of Th1 cells, or both and b. wherein improved IL-12 receptor signaling or increased proportion of Th1 cells indicates effectiveness of therapy. Therapy comprises any of the agents or combinations thereof described herein.

In one embodiment, a method for determining whether subject is a candidate for therapy with an agent that enhances a Th1 response, reduces a Th2 response, or the combination thereof, comprising the steps of a. incubating the subject's T cells with the agent and measuring the ratio or interferon-gamma-producing to IL-4 producing helper T cells, and b. wherein an increase in the ratio indicates potential effectiveness of therapy. Therapy comprises any of the agents or combinations thereof described herein.

In one embodiment, a method for determining whether therapy with an agent that enhances a Th1 response, reduces a Th2 response, or the combination thereof, is effective in a subject comprising determining the ratio of polyclonal Th1 to Th2 cells, wherein an increased ratio indicates improvement. Therapy comprises any of the agents or combinations thereof described herein.

In one embodiment, a method for determining whether therapy with an agent that enhances a Th1 response, reduces a Th2 response, or the combination thereof, is effective in a subject with disseminated coccidiomycosis, comprising determining the ratio of cocci-specific Th1 to Th2 cells, wherein an increased ratio indicates effectiveness. Therapy comprises any of the agents or combinations thereof described herein.

The following example is presented in order to more fully illustrate the preferred embodiments of the invention. It should in no way be construed, however, as limiting the broad scope of the invention.

EXAMPLES

Approvals. Written informed consent was obtained for human subjects research, as approved by the UCLA Institutional Review Board. Healthy donors were drawn from the donor pool of the UCLA Blood Bank, utterly deidentified, and purchased as whole blood through a service offered by the UCLA Virology Core.

Reagents and antibodies. Cells were grown and assayed in complete T-cell media, consisting of RPMI 1640 with L-glutamine (Gibco #11875) supplemented with 10% fetal bovine serum (Gibco #26140), 10 mM HEPES (Gibco #15630), 1× Pen/Strep (Gibco #15140), 1 mM sodium pyruvate (Gibco #11360) and 55 µM 2-mercaptoethanol (Gibco #21985). FACS buffer consisted of 1×DPBS (Gibco #14901) supplemented with 2% fetal bovine serum and 1 mM EDTA (ThermoFisher #15575). The following antibodies were used: anti-CD3ε (clone OKT3), anti-CD28 (clone CD28.2), anti-CD4 Brilliant Violet 421 and Alexa Fluor 647 (clone RPA-T4), anti-CD14 Brilliant Violet 421 (clone HCD14), anti-IFN-γ PE (clone 4S.B3), and Human TruStain FcX (Cat #422302) from Biolegend; anti-CD20 Brilliant Violet 421 (clone H1), anti-phospho-Stat1 (Tyr701) Alexa Fluor 488 (clone 4a), anti-phospho-Stat3 (Tyr705) Alexaxf Fluor 647 (clone 4/P-Stat3), anti-phospho-Stat4 (Tyr693) Alexa Fluor 647 (clone 38/P-Stat4), Mouse IgG2a Isotype Control Alexa Fluor 488 and Alexa Fluor 647 (clone MOPC-173), and anti-IL-4 PE-Cy7 (clone 8D4-8) from BD Biosciences. All antibodies were used at manufacturer-recommended dilutions in FACS experiments.

Recombinant human IL-12 p70 (Cat #200-12), IL-21 (Cat #200-21) and IFN-γ (Cat #300-02) were from Peprotech. Recombinant human IFN-α1 was from Cell Signaling Technology (Cat #8927). Anti-IL-4Rα (Dupilumab) for in vitro testing was obtained from the UCLA hospital pharmacy. Phorbol 12-myristate 13-acetate (PMA; Cat #P1585) and lipopolysaccharide (LPS; Cat #L4391) were from Sigma Aldrich. Ionomycin was from EMD Millipore (Cat #407953).

T-cell purification, activation and differentiation. CD4+ cells were purified from heparinized whole blood with the EasySep Direct Human CD4+ T Cell Isolation Kit (StemCell, Cat #19662). Twelve well plates were pre-coated with 1 µg/mL anti-CD3ε in PBS for 2 hr at 37° C. Cells were plated at 1 million per well in 1 mL complete T cell media supplemented with 2 µg/mL anti-CD28. For Th1 differentiation, 10 ng/mL IL-12 p70 was included in the culture. On day 3, CD4+ cells were removed from the anti-CD3ε coated wells and transferred to 6 well plates. Additional media supplemented with 100 U/mL IL-2 (and 10 ng/mL IL-12 p70 for the Th1 condition) was added to the wells. In some experiments, 50 µg/mL anti-IL-4Rα (dupilumab) was included in the cultures. On day 7, cells were harvested and assayed for cytokine production and pStat4 induction.

Phospho-Stat assays. For whole blood: 20 µL of 10X IL-21, IFN-γ, or IFN-α in PBS (or PBS only control) was added to 180 µL of blood in a 5 mL FACS tube to achieve a final concentration of 10 ng/mL. Tubes were incubated at 37° C. for 20 min, at which point 4 mL of pre-warmed 1× Lyse/Fix buffer (BD, Cat #558049) was added. Cells were fixed for 10 min at 37° C., centrifuged and washed twice with FACS buffer. For cultured cells: 50 µL of 10X IL-12 p70 in media (or media only control) was added to 1 million cells in 450 µL of complete T cell media to achieve a final concentration of 10 ng/mL. The cells were incubated at 37° C. for 20 min, and then an equal volume of pre-warmed Cytofix buffer (BD, Cat #554655) was added. Cells were fixed for 12 min at 37° C., centrifuged and washed twice with FACS buffer. Staining and permeabilization: Fc receptors were blocked for 5 min at RT, followed by a 20 min stain on ice with anti-CD4, anti-CD14 or anti-CD19. Cells were washed with FACS buffer and permeabilized for 30 min on ice with 1 mL Phosflow Perm Buffer III (BD, Cat #558050) that had been pre-cooled to −20° C. After permeabilization, two mL FACS buffer was added and the samples were centrifuged. After three additional washes, the cells were stained with anti-pStat4 or an isotype control for 30 min at RT. Samples were washed three times and data were collected on a Cytek DxP10 flow cytometer. Data were analyzed with FlowJo software.

Stimulation and intracellular cytokine staining. To stimulate cytokine production, 1 million CD4+ T cells were incubated in 1 mL complete T-cell media with or without 40 ng/mL PMA and 1 µM ionomycin for 5 hr at 37° C. For the final 4 hours, 1× Golgiplug (BD, Cat #555029) was added to all wells. Cells were harvested from the wells, washed with FACS buffer and fixed in 1 mL PBS/2% paraformaldehyde for 30 min at RT. After washing with FACS buffer, cells were permeabilized with FACS buffer containing 0.5% saponin. After blocking Fc receptors, the cells were stained with anti-cytokine antibodies for 30 min at RT and washed three times, all in the presence of saponin. Data were collected and analyzed as above.

For stimulation with Cocci antigen, frozen aliquots of PBMC were thawed and incubated for 24 hrs with 100 ng/mL LPS and 10 ug/mL T27K Cocci antigen. Golgiplug was included for the final 4 hrs of culture. Cells were harvested from the wells, stained for CD4, and then processed as above.

RNA sequencing. RNA was extracted from whole blood using the PAXgene Blood RNA Kit (Qiagen). Quantification and quality were assessed using Qubit 3.0 Fluorometer and Agilent bioanalyzer. 1 ug of total RNA was submitted to the UCLA Neuroscience Genomics Core (UNGC) for library construction and RNA sequencing. Sequencing libraries were generated using Illumina TruSeq Stranded Total RNA with Ribo-Zero Globin. Sequencing was performed to generate>65 million 120 base paired-end reads on the Illumina HiSeq 4000. FASTQ files were aligned to GRCh37 using STAR-2.5.2b with Gencode v19 annotation. Quality was assessed using RNA-SeQC v1.1.8. BAM files were analyzed in IGV to generate a sashimi plot of splice alterations.

IL12RB1 Isoforms. Splice junction data were downloaded from GTEx V7 (GTEx_Analysis_2016-01-15_v7_STARv2.4.2a_junctions.gct) or from an internal dataset of the IPH. Counts of the exon-exon junctions corresponding to both the long and short isoform for IL12RB1 were extracted (Junction IDs 19_18180524_18182921 and 19_18182144_18182921, respectively) for all whole blood samples (n=407). Twenty samples with a total read count of less than 10 across both junctions were excluded.

Case presentation. A previously healthy 4-year-old boy presented with fevers and a three-week history of enlarging subcutaneous nodules on his forehead. The physical exam was notable for three tender 3-5 cm masses on the forehead and scalp, a scaly plaque on the posterior neck, and tenderness in the right wrist and ankle. He had no prior history of recurrent or severe infections, and no family history of immune deficiency or autoimmunity. He lived in a *Coccidioides*-endemic region in California.

Imaging demonstrated a focal right lung consolidation, lymphadenopathy, and multiple osteolytic lesions in his skull, vertebral bodies, ribs, right radius, and right tibia (FIG. 1A). Surgical specimens from the skull lesions revealed fungal spherules that were confirmed as *Coccidioides* by PCR (FIG. 1B). Serologic tests showed *Coccidioides* IgG and IgM, which were absent in the cerebrospinal fluid. *Coccidioides* complement fixation titers were suggestive of disseminated disease, with activity detectable at the 1:32 dilution. The patient was treated with fluconazole and liposomal amphotericin B, and underwent surgical debridement of the most prominent osseous lesions (FIG. 1C). The spinal and radial lesions worsened as he developed new soft tissue lesions, which prompted additional debridement and escalation of antifungal therapy to posaconazole and high dose liposomal amphotericin B (7.5 mg/kg); sertraline was added for its putative antifungal activity. Complement fixation titers remained elevated at 1:256.

The rapid dissemination of his infection and young age prompted further investigation for an underlying immune defect. Initial workup ruled out HIV infection, and showed appropriate lymphocyte numbers, normal mitogen-induced lymphocyte proliferation, a normal level of IgM, and elevated IgG, IgA, and IgE (Table 1). We considered that cases of IFN-γR deficiency, STAT1 gain-of-function, STAT3 deficiency, and IL-12R deficiency have been described as contributing to monogenic susceptibility to coccidioidomycosis. To evaluate these possibilities, we stimulated monocytes and T cells with IFN-α and IFN-γ, which showed normal phosphorylation and, over time, dephosphorylation of STAT1 (FIG. 3A). STAT3 phosphorylation in response to IL-21 stimulation was also intact (FIG. 3B). These results suggested against defective signaling of IFN-γ, STAT1, or STAT3.

TABLE 1

Laboratory Data

| | Baseline (admission) | Reference Ranges |
|---|---|---|
| Lymphocyte Counts | | |
| CD3+ T lymphocytes | 2,193 (75%) | 1,400-3,700 (56-75%) |
| CD4+ T-cell helper subset | 1,235 (43%) | 700-2,200 (28-47%) |
| CD8+ Cytotoxic T cell subset | 842 (29%) | 490-1,300 (16-30%) |
| CD19+ B lymphocytes | 545 (19%) | 390-1,400 (14-33%) |
| NK lymphocytes | 141 (5%) | 130-720 (4-17%) |
| Immunoglobulins | | |
| IgG | 2,060 mg/dL | 540-1,330 mg/dL |
| IgA | 257 mg/dL | 30-160 mg/dL |

TABLE 1-continued

Laboratory Data

| | Baseline (admission) | Reference Ranges |
|---|---|---|
| IgM | 89 mg/dL | 40-140 mg/dL |
| IgE | 2,396 kIU/L | <20 kIU/L |
| Neutrophil oxidative burst | 96% positive | >90% positive |

To test IL-12 receptor function, we stimulated CD4+ T-cell blasts from the patient with IL-12. Compared to a healthy control, we observed very low numbers of cells responding to IL-12 with STAT4 phosphorylation (Control: 83%; Patient: 12% responding cells) (FIG. 1D). This result was not attributable to the absence of the receptor, as staining for IL-12Rβ1 (CD212) was similar to control (FIG. 3C). When cultured under neutral conditions, in vitro differentiation of CD4+ T cells to an IFN-γ-producing Th1 phenotype was severely impaired, while the proportion of IL-4-producing Th2 cells were greatly increased compared to healthy controls. (FIG. 1E). However, culturing under Th1 conditions (with exogenous IL-12) resulted in a 3-fold increase in the proportion of IFN-γ-producing cells (FIG. 1E), indicating that the IL-12 signaling defect could be overcome. We saw a similar excess of Th2 cells in specific responses to the *Coccidioides* antigen T27K (FIG. 1F) (Th1 to Th2 ratio of 0.41, subtracting background). In contrast, when stimulated with *Coccidioides* antigen, cells from an individual with a resolved case of Valley fever showed an almost exclusive Th1 response, as expected (FIGS. 6A-B).

We next examined the possibility of a previously described monogenic immunodeficiency as the cause for the observed defect in IL-12R signaling. Whole exome and genome sequencing revealed no plausible rare variants in or near the IL12RB1, IL12RB2, or TYK2 genes, or any primary immunodeficiency gene. No relevant structural variation was detected across the genome. Our patient did not have any of the polymorphic "RTR" variants (low functioning IL-12 receptor beta alleles) that confer susceptibility to infection. Because genome sequencing revealed no plausible rare exonic variants, RNA sequencing was employed to look for aberrant splicing as a cause of disease. Using this methodology, we identified the well-known short and long transcriptional isoforms of IL12RB1. Surprisingly, we found that 94% of our patient's transcripts (61 of 65 reads across the exon-exon junctions) comprised the short transcript, compared to an average of 67% in healthy controls (FIGS. 4A and B). We found no variants in or near the five poly-G tracts that promote splicing of the short isoform. Our subject thus produced aberrantly high levels of the short, non-functional isoform of IL12RB1, leading to impaired IL-12 signaling and Type-1 immunity.

Due to his progressive, refractory disease and the reported success of treatment with IFN-γ in a few patients with disseminated coccidioidomycosis, the patient was started on subcutaneous IFN-γ at a dose of 50 μg/m² on week 8 of admission. He tolerated treatment without significant adverse effects other than transient fevers, and he showed a decline in inflammatory markers (Table 2). However, his complement fixation titers remained elevated at 1:256. The dose of IFN-γ was gradually increased to 200m/m². We re-examined IL-12 signaling after treatment with IFN-γ, and noted a marked improvement in the IL-12R-mediated phosphorylation of STAT4 (FIG. 5A). Notably, the patient's initially defective response to IL-12 stimulation was not absolute, indicating that a latent ability to respond to IL-12 was awakened by IFN-γ therapy. The proportion of Th1 cells observed in vitro also increased after treatment with IFN-γ (FIG. 2B). The clinical disease, however, continued to progress, albeit at a slower pace, and he required additional surgical debridement of his radial lesion. The remaining calvarial lesions and the T3 spinal lesion continued to enlarge despite antifungal and IFN-γ therapies (FIG. 2A).

TABLE 2

Response to treatment

| | Baseline (admission) | Antifungals + IFN-γ | Antifungals + IFN-γ + Dupilumab |
|---|---|---|---|
| IgE (kIU/L) | 2,396 | 354 | 109 |
| IgG (mg/dL) | 2,190 | 2,060 | 1,350 |
| CRP | 9.5 | 3.0 (wk 10) | 1.0 (wk 20) |

Dupilumab is a monoclonal antibody that blocks the IL-4/IL-13 receptor. It is indicated for the treatment of severe asthma and atopic dermatitis and has an excellent safety profile. To date, dupilumab has not been used to promote clearance of infections. In vitro incubation of the patient's T cells with dupilumab resulted in an increase in the ratio of IFN-γ- to IL-4-producing helper T cells (FIG. 5B). In light of this finding and his refractory disease, dupilumab was added on week 16 of admission (starting at 2 mg/kg weekly, and up-titrated to 6 mg/kg weekly) without adverse effects. Signaling through the IL-4 receptor was utterly suppressed under this treatment regimen (FIG. 5C). Over time, the proportion of IL-4-producing T cells decreased, resulting in a 1:1 ratio of polyclonal Th1 to Th2 cells (FIGS. 2B and 5D) and *Coccidioides*-specific T cells improved their Th1 to Th2 ratio to 0.65 (46% increase over baseline). IgE levels also decreased significantly (Table 2). The complement fixation titers became undetectable and inflammatory markers normalized. Importantly, treatment with dupilumab plus IFN-γ resulted in dramatic clinical improvement followed by resolution of disease. Repeat imaging five weeks after the addition of dupilumab showed improvement of calvarial lesions for the first time, with complete resolution 11 weeks later (FIG. 2A). The T3 spinal lesion demonstrated resolution 15 weeks after dupilumab was added (FIG. 2A). The patient was discharged and remains on antifungals plus IFN-γ and dupilumab. Dupilumab was weaned to once weekly. At a one-year follow up visit, no new foci of infection were discovered. IFN-γ was decreased from four to three times per week. Transcriptional analysis of IL12RB1 showed the subject now demonstrated a normal splicing pattern (FIG. 4C).

A case of life-threatening, disseminated coccidioidomycosis (DCM) is described in a previously healthy child. Like most patients with DCM, this child lacked genomic evidence of any rare immune disease. However, comprehensive immunological testing showed an exaggerated production of IL-4 and reduced production of IFN-γ. Supplementation of antifungals with IFN-γ treatment slowed disease progression and the addition of IL-4/IL-13 blockade resulted in rapid clinical resolution. This report is the first to demonstrate that blocking Type-2 immunity can treat infection. This immunomodulatory approach could be used to enhance immune clearance of refractory fungal, mycobacterial, and viral infection.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for treating a disseminated or systemic *Coccidioides* fungal infection spread beyond the lungs in a subject in need thereof that is immunocompromised or has an immunodeficiency disease, comprising administering to the subject an agent that blocks IL-4 signaling.

2. The method of claim 1 wherein the disseminated or systemic fungal infection spread beyond the lungs is coccidioidomycosis.

3. The method of claim 1 wherein the subject is a pediatric subject.

4. The method of claim 1 wherein the agent is an IL-4 receptor antagonist.

5. The method of claim 1 wherein the agent is an IL-4 receptor alpha antagonist.

6. The method of claim 1 wherein the agent is an antibody or fragment thereof.

7. The method of claim 6 wherein the antibody or fragment thereof is a monoclonal antibody or fragment thereof.

8. The method of claim 6 wherein the agent is dupilumab, pascolizumab, lebrikizumab, anrukinzumab, or tralokinumab.

9. The method of claim 4 wherein the agent is pitrakinra.

10. The method of claim 1 wherein the subject is also administered interferon-gamma.

* * * * *